US010675488B2

(12) United States Patent
Deng et al.

(10) Patent No.: US 10,675,488 B2
(45) Date of Patent: *Jun. 9, 2020

(54) ACNE REMOVING SKIN CARE PRODUCT AND PREPARATION METHOD THEREOF

(71) Applicant: INFINITUS (CHINA) COMPANY LTD., Jiangmen, Guangdong (CN)

(72) Inventors: Wenjuan Deng, Guangdong (CN); Guangrong Liu, Guangdong (CN); Jian Tang, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/540,479

(22) PCT Filed: Jun. 24, 2016

(86) PCT No.: PCT/CN2016/087098
§ 371 (c)(1),
(2) Date: Jun. 28, 2017

(87) PCT Pub. No.: WO2017/036239
PCT Pub. Date: Mar. 9, 2017

(65) Prior Publication Data
US 2017/0354834 A1 Dec. 14, 2017

(30) Foreign Application Priority Data

Aug. 28, 2015 (CN) .......................... 2015 1 0540636

(51) Int. Cl.
*A61Q 19/00* (2006.01)
*A61K 36/752* (2006.01)
*A61K 8/9789* (2017.01)
*A61K 36/38* (2006.01)
*A61K 8/9783* (2017.01)
*A61K 36/53* (2006.01)

(52) U.S. Cl.
CPC ............ *A61Q 19/00* (2013.01); *A61K 8/9783* (2017.08); *A61K 8/9789* (2017.08); *A61K 36/38* (2013.01); *A61K 36/53* (2013.01); *A61K 36/752* (2013.01)

(58) Field of Classification Search
None
See application file for complete search history.

(56) References Cited

U.S. PATENT DOCUMENTS 9,993,510 B2* 6/2018 Liu ..................... A61K 47/46
2017/0348372 A1* 12/2017 Liu ..................... A61K 36/752

FOREIGN PATENT DOCUMENTS

| CN | 101428046 A | 5/2009 |
| CN | 101816687 A | 9/2010 |
| CN | 103202797 A | 7/2013 |
| CN | 104027270 A | 9/2014 |
| CN | 105168478 A | 12/2015 |
| CN | 105168479 A | 12/2015 |
| FR | 2504551 A1 | 10/1982 |
| JP | H07157412 A | 6/1995 |
| JP | H0859453 A | 3/1996 |
| JP | 2000044419 A | 2/2000 |
| JP | 2003231607 A | 8/2003 |
| JP | 2004161623 A | 6/2004 |
| JP | 2005200339 A | 7/2005 |
| WO | 2007002666 A2 | 1/2007 |
| WO | 2009/084200 A1 | 7/2009 |

OTHER PUBLICATIONS

Mohamed et al., "Single layer solar drying behaviour of Citrus aurantium leaves under forced convection," Energy Conversion and Management 46 (2005) 1473-1483.*
Mullaicharam et al., "Evaluation of Anti-Acne Property of Poly Herbal Formulation," Journal of Biomedical and Pharmaceutical Research 1 (3) 2012, 28-35.*
Pothitirat et al., "Comparison of bioactive compounds content, free radical scavenging and anti-acne inducing bacteria activities of extracts from the mangosteen fruit rind at two stages of maturity," Fitoterapia 80 (2009) 442-447.*
Acne Complex A100—Acne Control Oil—Laibo Cosmeceutical Technology (Shanghai) Co., Ltd., retrieved on Sep. 21, 2018 from http://laibo.com/cn/index.php?m=content&c=index&a=show&catid=87&id=81 (Copyright date—2002) pp. 1-2 (Year: 2002).*
Sepinov TM EMT 10—retrieved on Sep. 21, 2018 from https://www.seppic.com/sepinov-emt-10 pp. 1-3 (Year: 2018).*
International Search Report for PCT/CN2016/087098, dated Sep. 22, 2016, ISA/CN.
Liu, Xiang; "Natural Anti-acne Preparation", World Phytomedicines, vol. 10, No. 4, Dec. 31, 1995 (Dec. 31, 1995), pp. 166-170.
Liu, Jixin et al., "Observation of Bitter Orange Oil Inhibiting and Killing Human Demodex in vitro", Chinese Journal of Zoonoses, vol. 24, No. 5, Dec. 31, 2008 (Dec. 31, 2008), p. 485.
Sun, Changlei et al., "The clinical effect of anti-acne compound for acne treatment", Chinese Journal of Aesthetic Medicine, vol. 23, No. 1, Jan. 31, 2014 (Jan. 31, 2014), pp. 38-40.
First Office Action dated Aug. 28, 2018 for Japanese patent application No. 2017-541817, 6 pages, English translation provided by Global Dossier.
Chomnawang et al. "Effect of Garcinia mangostana on inflammation caused by Propionibacterium acnes" Fitoterapia, IDB Holding, Milan, IT, vol. 78,No. 6, Aug. 23, 2007, pp. 401-408.

(Continued)

*Primary Examiner* — Aradhana Sasan

(74) *Attorney, Agent, or Firm* — Yue (Robert) Xu; Apex Attorneys at Law, LLP

(57) ABSTRACT

Disclosed are an acne removal composition, a skin care product and a preparation method thereof, wherein the acne removal composition is made from *Garcinia mangostana* L pericarp, thyme and *Fructus aurantii*.

7 Claims, No Drawings

(56) References Cited

OTHER PUBLICATIONS

Yuangang Zu et al:"Activities of ten essential oils towards propionibacterium acnes and PC-3, A-549 and MCF-7 cancer cells", Molecules, vol. 15,No. 5,Apr. 30, 2010, pp. 3200-3210.

Tumane P M etal:"comparative study of antibacterial activity of peel extracts of citrus aurantium L.(lemon) against clinical isolates from wound infection",International Journal of Pharmaa and Bio Sciences January/ MA International Journal of Rharma and Bio Sicences Ind. vol. 5, No. 1, Jan. 2014, p. P382-387.

The European search report dated Mar. 21, 2019.

First Office Action dated Mar. 19, 2020 for Chinese patent application No. 201510540636.X, English translation provided by Global Dossier.

* cited by examiner

ACNE REMOVING SKIN CARE PRODUCT AND PREPARATION METHOD THEREOF

This application is the national phase of International Application No. PCT/CN2016/087098, titled "ACNE REMOVING SKIN CARE PRODUCT AND PREPARATION METHOD THEREOF", filed on Jun. 24, 2016, which claims the benefit of priority to Chinese Patent Application No. 201510540636.X titled "SKINCARE PRODUCT AND PREPARATION METHOD THEREOF", filed with the Chinese State Intellectual Property Office on Aug. 28, 2015, the entire disclosure of which application is incorporated herein by reference.

FIELD

The present invention relates to the field of cosmetics and skincare products, specifically to a skincare product and its preparation method, and in particular to an acne-removing skincare product and its preparation method thereof.

BACKGROUND OF THE INVENTION

Acne, also known as whelk, acne vulgaris, pimple), is a common skin disease which can cause inflammation of human skin sebaceous glands or hair follicles. Spine-shape papules, from which white or creamy white broken rice like juice can be squeezed out, are formed in local lesions. Acne often occurs in young people, in both sexes. It is more commonly found in male than in female, but the age of onset in female is earlier than in male. Acne occurs mostly in face, forehead, cheek and nasolabial fold, next in chest, back and shoulder. Usually, the skin damage caused by acne does not have subjective symptom. Pain may be accompanied under severe inflammation reactions. Acne can be classified into acne, papule, pustule and nodular cyst. Acne affects 80-90% of teenagers. After adolescence, *acnes* often can be abated automatically or cured, except that acne persists in some patients into their thirties. Although acne has a tendency of self-healing, the *acnes* themselves and scars caused by the *acnes* without timely treatment may severely affect the life quality of patient and cause mental pressure and financial burden of patients. Attentions should be paid to these problems.

The development of acne is mainly related to the factors, such as excessive sebum secretion, the duct clog of folliculosebaceous, bacteria infections and inflammation reactions. After people enter into their adolescence, the level of androgen, especially testosterone, is increased rapidly, promoting development of sebaceous glands and a large secretion of sebum. At the meantime, the abnormal follicular keratosis of the sebaceous gland ducts causes the clog of ducts, dyssebacia and the formation of keratotic plug (i.e. micro-acne). Various microbes, especially *Propionibacterium acnes*, overgrow in hair follicle. The lipases generated by *Propionibacterium acnes* degrade the sebum into free fatty acids, promote the chemotaxis of inflammatory cells and mediators, and finally induce and aggravate inflammation.

Acne can be divided into inflammatory acne and non-inflammatory acne. The excessive sebum secretion and the clog of hair follicle usually cause non-inflammatory acne, i.e., pimple, while the overgrowth of bacteria in the pimples will induce inflammation and cause inflammatory acne. When the damage to the skin caused by inflammatory acne reaches dermis layer, scars (pockmarks) form.

However, at present, the drugs used for acne treatment mostly contain hormones and antibiotics. Although they can reach the effect of acne removing, they have relatively obvious side-effects and strong dependence, thus are not suitable for long-term use. Currently commonly used acne-removing products in the market choose salicylic acid, capryloyl salicylic acid, ethanol, fruit acid and the like as the main active ingredients for disinfection and anti-inflammation, avoiding formation of inflammatory acne. However, the ingredients, such as salicylic acid, capryloyl salicylic acid, ethanol and fruit acid, have relatively high irritation and often cause side-effects such as skin sensitivity, sharp pain and severe decrustation. Also, toleration will develop after long-term use. Additionally, acne-removing products using traditional Chinese medicine extract as active ingredients also exist on the market, but they are too mild, work slowly and have poor effects.

SUMMARY OF THE INVENTION

In view of the above, the object of the present invention is to provide an acne-removing composition, skincare product and preparation method thereof.

To achieve the object of the invention, the following technical solution is adopted in the present invention:

An acne-removing composition is made from mangosteen (*Garcinia mangostana* L.) pericarp, thyme (*Thymus mongolicus* R.) and *Aurantii fructus*.

The acne-removing composition of the present invention is made from mangosteen pericarp, thyme and *fructus aurantii*. These medicines in the composition affect each other and have a synergic effect on anti-bacteria and anti-inflammation.

Herein, the scientific name of mangosteen is *Garcinia mangostana* L. The nature of mangosteen is warm and its taste is sweet and sour. It can tonify the spleen, promote the salivary secretion and stop diarrhea. The property of mangosteen pericarp is cool in nature and is bitter in taste, which has effects on anti-inflammation and pain relieving.

Thyme is also called *Thymus vulgaris, Thymus mongolicus* R., including thyme or Mongollian Thyme Herb (*Thymus przewalskii*), belonging to *Thymus* genus, Labiatae family. The whole plant is used as a medicine. To prepare the raw material, thyme is collected in summer when it is rich in leaves and branches. After the whole plant is cleaned and the root is removed (can be used for reproduction), it is cut into pieces and used freshly or after it is dried. The nature of thyme is slightly warm and it tastes spicy. It has the functions of dispelling wind to relieve exogenous syndrome, promoting qi circulation to relieve pain, stopping cough and reducing blood pressure. It is mainly used in the treatments of cold, cough, headache, toothache, dyspepsia, acute gastroenteritis and high blood pressure.

*Fructus aurantii* is the dried immature fruit of *Citrus aurantium* L. and its cultivated varieties. *Fructus aurantii* is harvested in July when the peel is still green, it is cut in half from the middle, dried in the air or at a low temperature. *Fructus aurantii* is bitter, spicy, sour and warm in nature. It has the functions of regulating qi and loosening center, activating stagnancy and relieving distension. It is mainly used in the treatments of Qi stagnation in chest and rib, swelling or pain, indigestion of food retention, congestion of fluid-retention, gastroptosis, archoptosis, uterine prolapse, and the like.

In some embodiments, the weight ratio of mangosteen pericarp, thyme and *Fructus aurantii* is (6 to 8):(1 to 2):(1 to 2).

Mangosteen pericarp, thyme and *Fructus aurantii* described in the present invention are well-known to those of ordinary skill in the art and commercially available by purchasing from the drugstores; or they can be cultured and collected through the method disclosed in the prior art, as long as they meet the national or industry standards.

A preparation method for the acne-removing composition is provided in the present invention, comprising: mixing mangosteen pericarp, thyme and *Fructus aurantii*; extracting with ethanol; collecting and purifying the extraction solution.

According to the present invention, in some embodiments, in the preparation method of the present invention, the ethanol extraction is performed by using 8 to 12 folds by weight of 76%-95% of ethanol-water solution for heating reflux extraction for 1 h-2.5 h.

According to the present invention, in some embodiments, the purification method described in the preparation method of the present invention, comprises steps of:
a. extraction solution is concentrated after filtration; the concentrated extract is dissolved in ethanol-water solution and refrigerated overnight; and
b. filtration is performed, the filtrate is adsorbed by macroporous adsorption resin and eluted by elution solution.

Herein, in some embodiments, in step a, the concentration is preferably conducted to a specific gravity of 1.05 to 1.1.

In some embodiments, in step a, the volume ratio of ethanol in the ethanol-water solution is 70%-80%.

Further, in some embodiments, the amount of ethanol-water solution used in step a is 4 to 6 folds by weight of that of the concentrated solution.

In some embodiments, in step a, the temperature for dissolving the concentrated solution in ethanol-water solution is 50° C. to 80° C.; and the dissolving duration is 0.5 h-2 h.

In some embodiments, in step a, the refrigeration overnight is performed by placing at 0° C. to 4° C. for 12 h-18 h.

According to the present invention, in some embodiments, in the preparation method of the present invention, in step b the elution is performed by eluting with water, 20%-40% ethanol-water solution, 60%-80% ethanol-water solution, successively, and the fragment eluted by 60%-80% ethanol-water solution is collected.

Herein, the amount of water used is 1 BV-2 BV, the amount of 20%-40% ethanol-water solution used is 1 BV-2 BV and the amount of 60%-80% ethanol used is 2 BV-4 BV.

In some embodiments, in step b, the elution is performed by eluting with water, 40% ethanol-water solution, 80% ethanol-water solution, and the fragment eluted by 80% ethanol-water solution is collected.

According to the present invention, in some embodiments, in the preparation method of the present invention, the fragment eluted by 60%-80% ethanol-water solution in step b is concentrated and dried. In some embodiments, the fragment is concentrated to a specific gravity of 1.05 to 1.1 and then spray drying is performed.

In some embodiments, in step b a further step of concentrating the solution after filtration is still comprised. It is preferred that the concentration step is conducted to a specific gravity of 1.05 to 1.1.

As appreciated by a person skilled in the art, the concentration in the preparation method of the present invention can be conducted by any known method in the art. In some specific examples, the concentration mentioned in the preparation method of the present invention is preferably reduced pressure concentration. The specific conditions are temperature of 60° C.-80° C., and vacuum degree≥0.08 Mpa.

According to different needs of a user, a person skilled in the art can prepare the acne-removing composition of the present invention into different dosage forms by adding various common excipients needed. The common preparations can be prepared through common formulation methods and processes. Herein the medicaments can be an external preparation that is well known in the field, such as liniment, ointment, cream, paste, film, coating, gel, aerosol, spray, patch, etc. Herein the cosmetics can be the well-known types, such as facial cream, emulsion, essence, facial mask, eye cream, basal solution, etc.

In some embodiments, the present invention provides an acne-removing skincare product, which contains the acne-removing composition described in the present invention.

In some embodiments, the acne-removing skincare product in the present invention also contains at least one of *Hedyotis diffusa Willd.*, *Radix Salvia miltiorrhiza*, *Caulis Lonicerae*, *Gleditsiae sinensis* seed and tea tree essential oil.

In some embodiments, the acne-removing skincare product in the present invention contains *Hedyotis diffusa Willd.*, *Radix Salvia Miltiorrhiza*, *Caulis Lonicerae*, *Gleditsia sinensis* seeds and tea tree essential oil.

*Hedyotis diffusa Willd.*, also named Spreading Hedyotis Herb, oldenlandia diffuse, is mainly into liver, kidney and small intestine meridian. It has functions of anti-cancer, detoxification, cooling down, relieving heat, eliminating blood stagnation and resolving carbuncle. It is used for the treatment of different cancers including nasopharyngeal carcinoma, lung carcinoma, breast cancer, esophagus cancer, gastric cancer, intestinal cancer, uterine carcinoma, malignant lymphoma, etc. *Hedyotis diffusa Willd.* also has functions of promoting blood circulation and swelling elimination, eliminating stagnation to stop pain, anti-inflammation and anti-bacterial. It has different degree of bacteriostasis and sterilization on both coccus and bacillus.

*Radix Salvia Miltiorrhiza*, also named red sage, purple *salvia* miltiorrhizae, has functions of promoting blood circulation to restore menstrual flow, removing stasis and relieving pain, cooling blood and eliminating carbuncle, clearing away heart trouble, nourishing the blood and tranquilizing the mind. It also has effect on vasodilation.

*Caulis Lonicera*, also called honeysuckle stein, is cold in nature and its taste is sweet. It has functions for clearing away heat and detoxification, and expelling wind and regulating meridian. It can be used in warm-heat diseases, carbuncle swollen boils, toxic heat and blood dysentery, and rheumatic fever. It also has effects of anti-bacterial, cough-relieving, expectoran, anti-asthma and anti-inflammation.

*Gleditsiae sinensis* seed is the seed of *Gleditsia sinensis* Lam., a plant of legume family. It has functions for moistening dryness, dispelling wind and swelling, and can be used to treat dry feces, intestinal wind bleeding, tenesmus and diarrhea, hernia, scrofula, swelling toxin, and Sores tinea. Furthermore, *Gleditsiae sinensis* seed contains plenty of chemical ingredients, such as terpenoids, flavonoids, phenolic acids and steroids, having effects of anti-bacteria, disinsection, anti-virus, anti-cancer and immuno-regulation.

Tea tree oil, also called *Melaleuca alternifolia* leaf oil, is a natural source of anti-bacteria ingredient. In particular, it has an excellent effect on microorganism which causes acne and vitiligo. It has an excellent anti-inflammation activity and can effectively reduce the symptoms including redness and swelling and inflammation caused by acne. It is gentle and safe for use.

*Hedyotis diffusa Willd., Radix Salvia Miltiorrhiza, Caulis Lonicerae, Gleditsia sinensis* seeds and tea tree essential oil described in the present invention are well-known to those of ordinary skill in the art and commercially available by purchasing from the drugstores; or they can be cultured and collected through the method disclosed in the prior art, as long as they meet the national or industry standards.

Additionally, *Hedyotis diffusa Willd., Radix Salvia Miltiorrhiza, Caulis Lonicerae*, and *Gleditsia sinensis* seed described herein can also be present as their individual extracts, such as *Hedyotis diffusa Willd*. extract, *Radix Salvia miltiorrhiza* extract, *Caulis Lonicerae* extract and *Gleditsia sinensis* seed extract. Those of ordinary skill in the art can understand that these extracts can be commercially purchased in the market or prepared by the methods disclosed in the prior art.

In some embodiments, the ratio by weight of the acne-removing composition: *Hedyotis diffusa Willd*. extract:*Radix Salvia miltiorrhiza* extract:*Caulis Lonicerae* extract:*Gleditsia sinensis* seed extract:tea tree essential oil in the acne-removing skincare product of the present invention is (1 to 5):(0.1 to 0.5):(0.1 to 0.5):(0.1 to 0.5):(0.1 to 0.5):(0.01 to 0.1).

It is known by those skilled in the art that "Acne-Removing Compound Preparation' can be made from *Hedyotis diffusa Willd., Radix Salvia miltiorrhiza, Caulis Lonicerae* and *Gleditsiae sinensis* seed. Thus in some other embodiments, the acne-removing skincare product described in the present invention comprises acne-removing compound preparation A100 and tea tree essential oil. The acne-removing compound preparation A100™ consists of the following components:

| Components | Amount |
| --- | --- |
| propylene glycol | 73.2% |
| water | 15% |
| OLDENLANDIA DIFFUSA extract | 2.5% |
| LONICERA JAPONICA extract | 3% |
| SALVIA MILTIORRHIZA ROOT extract | 2.5% |
| GLEDITSIA AUSTRALIS SEED extract | 3% |
| methylparaben | 0.1% |
| phenoxyethanol | 0.7%. |

Furthermore, in some embodiments of the present invention, the ratio by weight of the acne-removing composition: acne-removing compound preparation A100:tea tree essential oil in the acne-removing skincare product of the present invention is (1 to 5):(5 to 10):(0.01 to 0.1).

According to different needs of a user, those skilled in the art can prepare different dosage forms by adding various common excipients needed. The common skincare products, such as face cleaning milk, facial cream, emulsion, essence, facial mask, eyes cream, basal solution and the like, can be prepared through common formulation methods and processes.

In some embodiments, the acne-removing skincare product of the present invention further comprises at least one of solvent, thickener, conditioner, preservative, humectant, pH regulator, surfactant and freshener.

In some preferred embodiments, the acne-removing skincare product of the present invention is essence and the acne-removing skincare product further contains solvent, thickener, conditioner, preservative, humectant, pH regulator, surfactant and freshener.

In some embodiments, in the acne-removing skincare product of the present invention, said solvent is at least one of water, propylene glycol, butylene glycol, glycerol and pentylene glycol.

In some preferred embodiments, in the acne-removing skincare product of the present invention, said solvent is water and propylene glycol.

Furthermore, in some embodiments, the amount of the solvent used in the acne-removing skincare product of the present invention is 93 wt %-73 wt %.

In some embodiments, the amount of the solvent used in the acne-removing skincare product of the present invention is 80.64 wt %, in which the amount of water used is 74.64 wt % and the amount of propylene glycol used is 6 wt %.

In some embodiments, in the acne-removing skincare product of the present invention, said thickener is at least one of Carbomer™ and SEPINOV EMT-10™.

It will be understood by those skilled in the art that the Carbomer™ in the present invention can be any known Carbomer™, such as Carbomer U20™, Carbomer U21™ or Carbomer U10™.

In some preferred embodiments, in the acne-removing skincare product of the present invention, said thickeners are Carbomer U21™ and SEPINOV EMT-10™.

Carbomer U21™ is an acrylates/$C_{10}$-$C_{30}$ alkyl acrylate cross-linked polymer. SEPINOV EMT-10™ is a hydroxyethyl acrylate/sodium acryloyldimethyl taurate copolymer.

In some specific embodiments, the weight ratio of Carbomer U21™ and SEPINOV EMT-10™ is 1:3 to 3:1.

Further, in some embodiments, the amount of the thickener used in the acne-removing skincare product of the present invention is 1 wt %-2 wt %.

In some preferred embodiments, the amount of the thickener used in the acne-removing skincare product of the present invention is 1.65 wt %, wherein the amount of Carbomer U21™ used is 0.45 wt % and the amount of SEPINOV EMT-10™ used is 1.2 wt %.

In some embodiments, in the acne-removing skincare product of the present invention, said conditioner is at least one of allantoin, vitamin A palmitate, dipotassium glycyrrhizinate, *Centella asiatica* extract and nicotinamide.

In some preferred embodiments, in the acne-removing skincare product of the present invention, said conditioner is allantoin, vitamin A palmitate, dipotassium glycyrrhizinate and nicotinamide. Herein vitamin A palmitate is also named retinol palmitate. In some specific embodiments, the ratio by weight of allantoin, vitamin A palmitate, dipotassium glycyrrhizinate and nicotinamide is (0.1 to 0.3):(0 to 0.5):(0.1 to 0.3):(0.5 to 3).

In some preferred embodiments, in the acne-removing skincare product of the present invention, the conditioner is allantoin, dipotassium glycyrrhizinate and nicotinamide. In some specific embodiments, the ratio by weight of allantoin, dipotassium glycyrrhizinate, and nicotinamide is (0.1 to 0.3):(0.1 to 0.3):(0.5 to 3).

Further, in some embodiments, the amount of the conditioner used in the acne-removing skincare product of the present invention is 0.6 wt %-4.5 wt %.

Furthermore, in some specific embodiments, the amount of the conditioner used in the acne-removing skincare product of the present invention is 1.85 wt % wherein, the amount of allantoin used is 0.15 wt %, the amount of vitamin A palmitate used is 0.5 wt %, the amount of dipotassium glycyrrhizinate used is 0.2 wt % and the amount of nicotinamide used is 1 wt %.

In some specific embodiments, the amount of the conditioner used in the acne-removing skincare product of the present invention is 1.35 wt %, wherein the amount of allantoin used is 0.15 wt %, the amount of dipotassium glycyrrhizinate used is 0.2 wt % and the amount of nicotinamide used is 1 wt %.

In some embodiments, in the acne-removing skincare product of the present invention, said humectant is at least one of ethylhexylglycerin, butylene glycol, 1,2-pentylene glycol, glycerol, propylene glycol, sodium hyaluronate, D-panthenol and sodium pyrrolidone carboxylate.

In some preferred embodiments, in the acne-removing skincare product of the present invention, the humectant is butylene glycol and 1,2-pentylene glycol.

In some specific embodiments, the weight ratio of butylene glycol and 1,2-pentylene glycol is 4:1.

Further, in some embodiments, in the acne-removing skincare product of the present invention, the amount of the humectant used is 2 wt %-3 wt %.

In some preferred embodiments, the amount of the humectant used in the acne-removing skincare product of the present invention is 2.5 wt %, wherein the amount of butylene glycol used is 2 wt % and the amount of 1,2-pentylene glycol used is 0.5 wt %.

In some embodiments, in the acne-removing skincare product of the present invention, the pH regulator is at least one of sodium hydroxide, potassium hydroxide, arginine, citric acid and sodium citrate.

In some preferred embodiments, in the acne-removing skincare product of the present invention, said pH regulator is sodium hydroxide.

Further, in some embodiments, in the acne-removing skincare product of the present invention, the amount of the pH regulator used is 0.1 wt %-0.2 wt %.

In some preferred embodiments, in the acne-removing skincare product of the present invention, the amount of the pH regulator used is 0.15 wt %.

In some embodiments, in the acne-removing skincare product of the present invention, said surfactant is at least one of tween-20, PEG-40 hydrogenated castor oil and PEG-60 hydrogenated castor oil.

In some preferred embodiments, in the acne-removing skincare product of the present invention, said surfactant is tween-20.

Herein, tween-20 is also named polysorbate-20.

Further, in some embodiments, in the acne-removing skincare product of the present invention, the amount of the surfactant used is 0.1 wt %-1 wt %.

In some preferred embodiments, in the acne-removing skincare product of the present invention, the amount of the surfactant used is 0.6 wt %.

In some embodiments, in the acne-removing skincare product of the present invention, said freshener is at least one of cooling complex, menthol, mint essential oil and menthol lactate.

In some preferred embodiments, in the acne-removing skincare product of the present invention, the freshener is Cooling Complex.

Herein, Cooling Complex is obtained by extraction from leaves of rosemary, *Melissa axillaries* and mint.

Further, in some embodiments, in the acne-removing skincare product of the present invention, the amount of the freshener used is 0.01 wt %-0.1 wt %.

In some preferred embodiments, in the acne-removing skincare product of the present invention, the amount of the freshener used is 0.05 wt %.

In some specific embodiments, the acne-removing skincare product of the present invention comprises:

| | |
|---|---|
| the acne-removing composition of the present invention | 1 wt %-5 wt % |
| acne-removing compound preparation A100 ™ | 2 wt %-10 wt % |
| tea tree essential oil | 0.06 wt % |
| carbomer U21 ™ | 0.45 wt % |
| SEPINOV EMT-10 ™ | 1.2 wt % |
| allantoin | 0.1 wt %-0.3 wt % |
| vitamin A palmitate | 0 wt %-0.5 wt % |
| dipotassium glycyrrhizinate | 0.1 wt %-0.3 wt % |
| *Centella asiatica* extract | 0 to 0.5 wt % |
| nicotinamide | 0.5 wt %-3 wt % |
| butylene glycol | 1 wt %-5 wt % |
| pentylene glycol | 0.5 wt %-3 wt % |
| sodium hydroxide | 0.15 wt % |
| tween-20 | 0 to 1 wt % |
| cooling complex | 0 to 0.1 wt % |
| propylene glycol | 0 to 8 wt % |
| water | making up to 100 wt % |

The dose and regimen for the acne-removing composition and the acne-removing skincare product of the present invention depend on many factors, including age, weight, sex, health status and nutrition status of the user, activity intensity of the compound, duration, metabolic rate, severity of the disease and the judgment of the doctor. A person skilled in the art can easily decide the dose and regime of the acne-removing composition and the acne-removing skincare product of the present invention.

The present invention also provided a method for preparing the acne-removing skincare product, comprising following steps:

1) Carbomer U21™, allantoin and allantoin are taken and dissolved completely by adding water, then heated to 70° C.~95° C. to obtain a first reaction solution.

2) acne-removing compound preparation A100 and the acne-removing composition of the present invention are dissolved by adding water and propylene glycol, respectively, then added into the first reaction solution at 80° C., mixed to dissolved completely to obtain a second reaction solution;

3) sodium hydroxide is added to the second reaction solution, and mixed evenly at 80° C. to obtain a third reaction solution;

4) butylene glycol and vitamin A palmitate are added to the third reaction solution and mixed evenly, the temperature is reduced to 45° C., and a forth reaction solution is obtained;

5) pentylene glycol, cooling complex and tea tree essential oil are mixed and dissolved, then added into the forth reaction solution, mixed evenly, to obtain a fifth reaction solution; and 6) dipotassium glycyrrhizinate, *Centella asiatica* extract and nicotinamide are dissolved by adding water, then added into the fifth reaction solution, and mixed evenly.

Herein, in some embodiments, the mixing in step 2) of the preparation method is stirring and homogenizing to dissolve the materials thoroughly without opaque particles presented. Preferably, the duration for the homogenization is 2 minutes.

In some embodiments, the dissolving in step 5) of the preparation method is specifically performed by heating to 85° C. and dissolving thoroughly by stirring.

In some embodiments, after the mixing in step 6) of the preparation method, a homogenizing step is further included. Preferably, the duration for the homogenization is 2 minutes.

The acne-removing composition of the present invention consists of mangosteen pericarp, thyme and *fructus aurantii*. It is proved by *Propionibacterium acnes* inhibition test that this Chinese medicine composition has excellent inhibition effect on *Propionibacterium acnes* growth. Also, these three raw materials have a synergic effect on anti-inflammation. They work rapidly and have an excellent effect. The acne-removing skincare product of the present invention contains the acne-removing composition of the present invention and components such as *Hedyotis diffusa Willd., Radix Salvia miltiorrhiza, Caulis Lonicerae, Gleditsiae sinensis* seed and tea tree essential oil, does not contain ethanol, thus it is gentle and safe for use. The experiments demonstrate that the acne-removing skincare product of the present invention has an excellent effect and high cure rate for acne. It is natural, gentle and suitable for long-term use. The preparation method for the acne-removing skincare product of the present invention is easy to be handled and suitable for large-scale production.

DETAILED DESCRIPTION OF EMBODIMENTS

Hereinafter, the technical solutions in the examples of the present invention will be described clearly and completely in conjunction with examples of the present invention. It is apparent that the described examples are merely a part of the examples of the present invention rather than all. Based on the examples of the present invention, all other examples obtained by a person skilled in the art without creative work are within the scope of the present invention.

To further understand the present invention, detailed descriptions are provided in combination with the following examples.

Example 1: An Acne-Removing Composition of the Present Invention

1. Mangosteen pericarp, thyme and *Fructus aurantii* were crushed respectively, passed through a 60-mesh sieve, and mixed in a ratio of 80 g mangosteen pericarp, 20 g thyme and 20 g *Fructus aurantii;*

2. reflux extraction was performed for 2.5 h by using 95% ethanol-water solution in a amount of 12 folds by weight of the raw materials;

3. the above extraction solution was filtered through 100-mesh filter cloth to remove the residue, concentrated under reduced pressure (temperature 60° C.-80° C., vacuum degree≥0.08 Mpa, the same below) to obtain 72 g concentrated solution with a specific gravity of 1.08;

4. recycled ethanol-water solution was adjusted to a concentration of 80%, added to the concentrated solution at a volume ratio of 6:1 (ethanol-water solution:concentrated solution); stirred and dissolved at 80° C. for 2 h, and refrigerated overnight at 4° C. for 18 h;

5. the refrigerated solution was filtered and the filtrate was concentrated under reduced pressure to obtain 40 g product with a specific gravity of 1.08;

6. the concentrated solution was adsorbed by polyamide resins and eluted with water, 40% ethanol-water solution, 80% ethanol-water solution respectively, wherein the amount of water used is 1 BV, the amount of 40% ethanol-water solution used is 1 BV, and the amount of 80% ethanol-water solution used is 4B V;

7. a fragment eluted by 80% ethanol-water solution was collected and concentrated under reduced pressure to a specific gravity of 1.06, followed by spay drying to obtain 5.04 g.

Example 2: An Acne-Removing Composition of the Present Invention

1. Mangosteen pericarp, thyme and *Fructus aurantii* were crushed respectively, passed through a 60-mesh sieve, and mixed in a ratio of 60 g mangosteen pericarp, 10 g thyme and 10 g *Fructus aurantii;*

2. reflux extraction was performed for 1 h by using 60% ethanol-water solution in an amount of 8 folds by weight of the raw materials;

3. the above extract was filtered through 100-mesh filter cloth to remove the residue, concentrated under reduced pressure (temperature 60° C.-80° C., vacuum degree≥0.08 Mpa, the same below) to obtain 106 g concentrated solution with a specific gravity of 1.08;

4. recycled ethanol-water solution was adjusted to a concentration of 60%, added to the concentrated solution at a volume ratio of 4:1 (ethanol-water solution:concentrated solution); stirred and dissolved at 50° C. for 0.5 h, and refrigerated overnight at 0° C. for 12 h;

5. the refrigerated solution was filtered and the filtrate was concentrated under reduced pressure to obtain 76 g product with a specific gravity of 1.08;

6. the concentrated solution was adsorbed by polyamide resins and eluted with water, 40% ethanol-water solution, 80% ethanol-water solution respectively, wherein the amount of water used is 2 BV, the amount of 40% ethanol-water solution used is 2 BV, and the amount of 80% ethanol-water solution used is 2 BV;

7. a fragment eluted by 80% ethanol-water solution was collected and concentrated under reduced pressure to a specific gravity of 1.06, followed by spay drying to obtain 3.2 g.

Example 3: An Acne-Removing Composition of the Present Invention

1. Mangosteen pericarp, thyme and *Fructus aurantii* were crushed respectively, passed through a 60-mesh sieve, and mixed in a ratio of 80 g mangosteen pericarp, 10 g thyme and 10 g *Fructus aurantii;*

2. reflux extraction was performed for 2 h by using 75% ethanol-water solution in a amount of 10 folds by weight of the raw materials;

3. the above extract was filtered through 100-mesh filter cloth to remove the residue, concentrated under reduced pressure (temperature 60° C.-80° C., vacuum degree≥0.08 Mpa, the same below) to obtain 106 g concentrated solution with a specific gravity of 1.06;

4. recycled ethanol-water solution was adjusted to a concentration of 70%, added to the concentrated solution at a volume ratio of 5:1 (ethanol-water solution:concentrated solution); stirred and dissolved at 60° C. for 1 h, and refrigerated overnight at 2° C. for 15 h;

5. the refrigerated solution was filtered and the filtrate was concentrated under reduced pressure to obtain 76 g product with a specific gravity of 1.08;

6. the concentrated solution was adsorbed by polyamide resins and eluted with water, 40% ethanol-water solution, 80% ethanol-water solution respectively, wherein the amount of water used is 1 BV, the amount of 40% ethanol-water solution used is 2 BV, and the amount of 80% ethanol-water solution used is 3 BV;

7. a fragment eluted by 80% ethanol-water solution was collected and concentrated under reduced pressure to a specific gravity of 1.06, followed by spay drying to obtain 4.4 g.

Comparative Example 1

1. 100 g Mangosteen pericarp was crushed, and passed through a 60-mesh sieve;
2. reflux extraction was performed for 2 h by using 75% ethanol-water solution in a amount of 10 folds by weight of the raw materials;
3. the above extract was filtered through 100-mesh filter cloth to remove the residue, concentrated under reduced pressure (temperature 60° C.-80° C., vacuum degree≥0.08 Mpa, the same below) to obtain 62 g concentrated solution with a specific gravity of 1.06;
4. recycled ethanol-water solution was adjusted to a concentration of 70%, added to the concentrated solution at a volume ratio of 5:1 (ethanol-water solution:concentrated solution); stirred and dissolved at 60° C. for 1.5 h, and refrigerated overnight at 2° C. for 15 h;
5. the refrigerated solution was filtered and the filtrate was concentrated under reduced pressure to obtain 54 g product with a specific gravity of 1.08;
6. the concentrated solution was adsorbed by polyamide resins and eluted with water, 40% ethanol-water solution, 80% ethanol-water solution respectively, wherein the amount of water used is 1 BV, the amount of 40% ethanol-water solution used is 2 BV, and the amount of 80% ethanol-water solution used is 3 BV;
7. a fragment eluted by 80% ethanol-water solution was collected and concentrated under reduced pressure to a specific gravity of 1.08, followed by spay drying to obtain 4.0.

Comparative Example 2

1. 100 g thyme was crushed, and passed through a 60-mesh sieve;
2. reflux extraction was performed for 2 h by using 75% ethanol-water solution in a amount of 10 folds by weight of the raw materials;
3. the above extract was filtered through 100-mesh filter cloth to remove the residue, concentrated under reduced pressure (temperature 60° C.-80° C., vacuum degree≥0.08 Mpa, the same below) to obtain 52 g concentrated solution with a specific gravity of 1.06;
4. recycled ethanol-water solution was adjusted to a concentration of 70%, which was added to the concentrated solution at a volume ratio of 5:1 (ethanol-water solution: concentrated solution); stirred and dissolved at 60° C. for 1.5 h, and refrigerated overnight at 2° C. for 15 h;
5. the refrigerated solution was filtered and the filtrate was concentrated under reduced pressure to obtain 38 g product with a specific gravity of 1.08;
6. the concentrated solution was adsorbed by polyamide resins and eluted with water, 40% ethanol-water solution, 80% ethanol-water solution respectively, wherein the amount of water used is 1 BV, the amount of 40% ethanol-water solution used is 2 BV, and the amount of 80% ethanol-water solution used is 3 BV;
7. a fragment eluted by 80% ethanol-water solution was collected and concentrated under reduced pressure to a specific gravity of 1.06, followed by spay drying to obtain 1.2 g.

Comparative Example 3

1. 100 g *Fructus aurantii* was crushed, and passed through a 60-mesh sieve;
2. reflux extraction was performed for 2 h by using 75% ethanol-water solution in a amount of 10 folds by weight of the raw materials;
3. the above extract was filtered through 100-mesh filter cloth to remove the residue, concentrated under reduced pressure (temperature 60° C.-80° C., vacuum degree≥0.08 Mpa, the same below) to obtain 70 g concentrated solution with a specific gravity of 1.06;
4. recycled ethanol-water solution was adjusted to a concentration of 70%, added to the concentrated solution at a volume ratio of 5:1 (ethanol-water solution:concentrated solution); stirred and dissolved at 60° C. for 1.5 h, and refrigerated overnight at 2° C. for 15 h;
5. the refrigerated solution was filtered and the filtrate was concentrated under reduced pressure to obtain 58 g product with a specific gravity of 1.08;
6. the concentrated solution was adsorbed by polyamide resins and eluted with water, 40% ethanol-water solution, 80% ethanol-water solution respectively, wherein the amount of water used is 1 BV, the amount of 40% ethanol-water solution used is 2 BV, and the amount of 80% ethanol-water solution used is 3 BV;
7. a fragment eluted by 80% ethanol-water solution was collected and concentrated under reduced pressure to a specific gravity of 1.05, followed by spay drying to obtain 1.8 g.

Experimental Example 1: Bacteriostasis Effect

1. Materials
1.1 Test bacterial strain: *Propionibacterium acnes* (ATCC6919)
1.2 Chinese medicine composition samples: D1, D2, D3, D4, D5 and D6, stored at 4° C. for use, wherein samples D1 to D6 correspond to the products prepared by Examples 1, 2 and 3, and Comparative examples 1, 2 and 3, respectively.
1.3 Culture medium: *Propionibacterium acnes* culture medium (pH was adjusted to 6.6 to 7.0). Agar was added in 15 g per liter to the solid culture medium.
2. Methods
2.1 Preparation of bacteria suspension and inoculation
 0.1 ml frozen deposit bacteria suspension was added to 5 ml *Propionibacterium acnes* culture medium and cultured at 37° C. under anaerobic condition for 2 days, thus the bacteria suspension for the experiment was obtained.
2.2 Preparation of sample solutions
 Samples D1, D2, D3, D4, D5 and D6 were diluted in saline to the test concentration of 0.1%, followed by gradient dilution, respectively. In the first test, the gradient concentrations were 100% (original sample solution), 50%, 25%, 12.5%, 6.25%, 3.125%, 1.56% and 0.78%, respectively. In the second test, the gradient diluted concentrations for second test were 10%, 8%, 6%, 4% and 2%, respectively.
2.3 Preparation of bacteria suspension
 The bacteria suspension was diluted in *Propionibacterium acnes* culture medium to a final concentration of $10^6$ CFU/ml.
2.4 Culture and result judgement
 100 μL bacteria suspension and 100 μL sample solution were added to the well. The negative control without adding bacteria and the normal growth control without adding test solution were set at the same time. Each sample was performed in triplicate and the average was taken. Results were observed after anaerobic incubation at 37° C. for 48 h. The presence of turbidity was judged by naked eye and data were read out directly. The prerequisites for result judgement were: the growth control is well, there is no bacteria and the growth is clear for the blank control, and the growth of bacteria in other wells was inhibited with the increasing gradient concentrations of the drugs.

TABLE 1

Results of the first bacteriostasis test in gradient concentrations

| Gradient Concentrations | D1 | D2 | D3 | D4 | D5 | D6 |
|---|---|---|---|---|---|---|
| 50% | − | − | − | − | − | − |
| 25% | − | − | − | − | + | + |
| 12.5% | − | − | − | + | + | + |
| 6.25% | + | + | + | + | + | + |
| 3.125% | + | + | + | + | + | + |
| 1.56% | + | + | + | + | + | + |
| 0.78% | + | + | + | + | + | + |

Note:
+ means presence of bacteria growth;
− means no bacteria growth.

TABLE 2

Results of the second bacteriostasis test by gradient concentrations

| Gradient Concentrations | D1 | D2 | D3 | D4 |
|---|---|---|---|---|
| 10% | − | − | − | + |
| 8% | − | + | − | + |
| 6% | + | + | + | + |
| 4% | + | + | + | + |
| 2% | + | + | + | + |
| 1% | + | + | + | + |

Note:
+ means presence of bacteria growth;
− means no bacteria growth.

2.5 Results

It can be found from the results in Table 1 that the solutions from the three examples with a concentration of 0.1% all had good growth inhibition on *Propionibacterium acnes* when they were diluted to 12.5% or higher concentrations. However, in comparative samples, a desirable effect can be achieved when the concentration of the diluted solutions is 25% or higher for D4 and the concentration is 50% or higher for D5 and D6. It can be found from the results in Table 2, after verification, the bacteriostasis effect can be achieved by D1 and D3 at a concentration of 8%, and by D2 at a concentration of 10%.

It can be known from the above results that minimal addition of the composition product of the present invention in about 0.01% can achieve basically the inhibition effect on *Propionibacterium acnes*. Also, the composition of the present invention has a stronger bacteriostasis effect than the medicinal material used solely.

Example 4: An Acne-Removing Skincare Product of the Present Invention

Formula:

| | |
|---|---|
| Acne-removing composition in example 1 | 2 wt % |
| Acne-removing compound preparation A100 ™ | 10 wt % |
| Tea tree essential oil | 0.06 wt % |
| Carbomer U21 ™ | 0.45 wt % |
| SEPINOV EMT-10 ™ | 1.2 wt % |
| Allantoin | 0.15 wt % |
| Vitamin A palmitate | 0.5 wt % |
| Dipotassium glycyrrhizinate | 0.2 wt % |
| Nicotinamide | 1 wt % |
| Butylene glycol | 2 wt % |
| Pentylene glycol | 0.5 wt % |
| Sodium hydroxide | 0.15 wt % |
| tween-20 | 0.6 wt % |
| cooling complex | 0.05 wt % |
| Propylene glycol | 6 wt % |
| Water | making up to 100 wt % |

Preparation Method:

1) Carbomer U21™ and allantoin are taken and dissolved completely by adding water, then heated to 80° C. to obtain the first reaction solution.

2) acne-removing compound preparation A100™ and the acne-removing composition of the present invention are dissolved by adding water and propylene glycol, respectively, then added into the first reaction solution, stirred at 80° C. and homogenized to dissolve the raw material completely to obtain the second reaction solution;

3) sodium hydroxide is added to the second reaction solution, and mixed evenly at 80° C. to obtain the third reaction solution;

4) Butylene glycol and vitamin A palmitate are added to the third reaction solution and mixed evenly, the temperature is reduced to 45° C., and the forth reaction solution is obtained;

5) Pentylene glycol, cooling complex and tea tree essential oil are mixed, heated to 85° C., stirred to be dissolved completely, then added into the forth reaction solution, mixed evenly, to obtain the fifth reaction solution; and 6) Dipotassium glycyrrhizinate, and nicotinamide are dissolved by adding water, then added into the fifth reaction solution, and mixed evenly.

Example 5: An Acne-Removing Skincare Product of the Present Invention

Formula:

| | |
|---|---|
| The acne-removing composition in example 2 | 2 wt % |
| Acne-removing compound preparation A100 ™ | 10 wt % |
| Tea tree essential oil | 0.06 wt % |
| Carbomer U21 ™ | 0.45 wt % |
| SEPINOV EMT-10 ™ | 1.2 wt % |
| Allantoin | 0.15 wt % |
| Dipotassium glycyrrhizinate | 0.2 wt % |
| Nicotinamide | 1 wt % |
| Butylene glycol | 2 wt % |
| Pentylene glycol | 0.5 wt % |
| Sodium hydroxide | 0.15 wt % |
| tween-20 | 0.6 wt % |
| cooling complex | 0.05 wt % |
| Propylene glycol | 6 wt % |
| Water | making up to 100 wt % |

Preparation Method:

1) Carbomer U21™, allantoin and SEPINOV EMT-10™ are taken and dissolved completely by adding water, then heated to 80° C. to obtain the first reaction solution.

2) acne-removing compound preparation A100™ and the acne-removing composition of the present invention are dissolved by adding water and propylene glycol, respectively, then added into the first reaction solution, stirred at 80° C. and homogenized to dissolve the raw material completely to obtain the second reaction solution;

3) sodium hydroxide is added to the second reaction solution, and mixed evenly at 80° C. to obtain the third reaction solution;

4) Butylene glycol is added to the third reaction solution and mixed evenly, the temperature is reduced to 45° C., and the forth reaction solution is obtained;

5) Pentylene glycol, cooling complex and tea tree essential oil are mixed, stirred to be dissolved complelety, then added into the forth reaction solution, mixed evenly, to obtain the fifth reaction solution; and 6) Dipotassium glycyrrhizinate and nicotinamide are dissolved by adding water, then added into the fifth reaction solution, and mixed evenly.

Example 6: Effect in Use of the Skincare Product of the Present Invention

1. Test samples: the acne-removing skincare product of Example 4 and the acne-removing skincare product of Example 5

2. Subjects: not less than 12-year old in age; female:male≈1:1.

IGA (Investigator Global Assessment) grade 2: 12~25 years old, 15 people; over 25 years old, 15 people.

IGA grade 3: 12~25 years old, 15 people; over 25 years old, 15 people.

3. Test area: whole face

4. Use method: used for 5 days and 28 days; at least twice a day for acne and twice a day for pockmark.

Treatment in respect to acne: after cleaning the skin, rice-size skincare product was extruded and coated gently around the acne, at least twice daily. For severe acne, number of application can be appropriately increased. Stop using other acne-removing products two weeks prior to the test.

Treatment in respect to pockmark: after cleaning the skin, rice-size skincare product was extruded and coated gently around the pockmark, twice daily. Stop using other acne-removing products two weeks prior to the test.

5. Test time points: before using the product (Day0), 5 days after using the product (Day5), and 28 days after using the product (Day28)

6. Test parameters:

After cleaning their faces, the subjects relaxed in the lab (temperature 21±1° C., relative humidity 50±5%) for 20 minutes, expert evaluation and self evaluation on the whole face were carried out before using the product (Day0), 5 days after using the product (Day5), and 28 days after using the product (Day28), respectively. The contents of melanin and heme in skin were assayed by instruments 28 days after using the product.

1. Expert Evaluation

A. IGA grading (comprehensive evaluation according to the new/old acne on the whole face)

Grade 0: no inflammatory skin lesions (papule, pustule, nodule, cyst), no non-inflammatory skin lesions (blackhead, whitehead)

Grade 1: rare non-inflammatory skin lesions, one or no small inflammatory skin lesion Grade 2: slight skin lesions; worse than grade 1; some non-inflammatory skin lesions and a few inflammatory skin lesions (only papules and pustules, no nodules)

Grade 3: moderate skin lesions; worse than grade 2; many non-inflammatory skin lesions, maybe some inflammatory skin lesions, but one or no nodule Grade 4: severe skin lesions; worse than grade 3; many non-inflammatory and inflammatory skin lesions, a few nodules B. Skin lesion counting: count the non-inflammatory and inflammatory skin lesions before and after using the products, respectively.

C. Pockmark fading analysis: score the skin evenness, clearness and brightness before and after using the products, respectively. (5-point scale: 1=minor, 5=very obvious)

D. Severity of inflammatory skin lesions (papule, pustule, nodule, cyst) analysis (evaluation according to the old acne on the whole face on photos):

Grade 0: no inflammatory skin lesions (papule, pustule, nodule, cyst)

Grade 1: one or no small inflammatory skin lesion

Grade 2: slight skin lesions; worse than grade 1; a few inflammatory skin lesions (only papule and pustule, no nodule)

Grade 3: moderate skin lesions; worse than grade 2; maybe some inflammatory skin lesions, but one or no nodule Grade 4: severe skin lesions; worse than grade 3; many inflammatory skin lesions, some nodules 2. Self-Evaluation of Subjects by Using Questionnaire Survey After the use of product for 5 days and 28 days, questionnaire survey was carried out in respect to satisfaction of acne-removing.

3. Skin Melanin and Heme Assay

Skin melanin and heme assay was conducted by using detector Mexameter MX18 to detect the content of melanin and heme in skin.

7. Data Statistics

Data statistics was performed by SPSS13.0 for windows software. The difference between before and after the test was compared by rank sum test, and the significance level is p≤0.05.

8. Test Results

1. IGA Grading

After the use of test products for 28 days, the severity of skin lesions in IGA2 and IGA3 subjects were observed. The results were shown in Table 3.

TABLE 3

| | | | Grade 0 | Grade 1 | Grade 2 | Grade 3 | Grade 4 |
|---|---|---|---|---|---|---|---|
| test samples | | | | | | | |
| the acne-removing skincare product of Example 4 | IGA2 group | Day 0 | 0 | 0 | 30 | 0 | 0 |
| | | Day 28 | 5 | 5 | 20 | 0 | 0 |
| | IGA3 group | Day 0 | 0 | 0 | 30 | 0 | 0 |
| | | Day 28 | 5 | 5 | 20 | 0 | 0 |
| the acne-removing skincare product of Example 5 | IGA2 group | Day 0 | 0 | 0 | 30 | 0 | 0 |
| | | Day 28 | 5 | 7 | 18 | 0 | 0 |
| | IGA3 group | Day 0 | 0 | 0 | 0 | 30 | 0 |
| | | Day 28 | 2 | 0 | 22 | 6 | 0 |

The changes of IGA grade

As shown in Table 3, 28 days after the use of the acne-removing skincare product of Example 4, in IGA2 group, there were 10 people who had improvement in their skin lesions with grade 0 or grade 1 of severity of skin lesion symptoms or with two grades of improvement in severity, compared with basal values. The effective improvement rate was 33.3%. In IGA3 group, there were 0 people who had improvement in their skin lesions with grade 0 or grade 1 of severity of skin lesion symptoms or with two grades of improvement in severity, and the effective improvement rate was 0%. 28 days after the use of the acne-removing skincare product of Example 5, in IGA2 group, there were 12 people who had improvement in their skin lesions with grade 0 or grade 1 of severity of skin lesion symptoms or with two grades of improvement in severity, and the effective improvement rate was 40.0%. In IGA3 group, there were 2 people who had improvement in their skin lesions with grade 0 or grade 1 of severity of skin lesion symptoms or with two grades of improvement in severity, and the effective improvement rate was 6.7%.

2. Skin Lesion Counting

Non-inflammatory skin lesions and inflammatory skin lesions were counted before and after the use of test samples. Non-inflammatory skin lesions and inflammatory skin lesions before and after 5 days of use of the product were counted for the subjects in IGA2 and IGA3 groups. The results were shown in Table 4.

TABLE 4

Skin lesion counting

| Test samples | | | nodule | cyst | papule | pustule | blackhead | whitehead |
|---|---|---|---|---|---|---|---|---|
| the acne-removing skincare product of Example 4 | IGA2 group | Day 0 | 0.00 | 0.00 | 4.47 | 0.10 | 1.97 | 0.23 |
| | | Day 5 | 0.00Δ | 0.00Δ | 3.47Δ | 0.13Δ | 0.70* | 0.20Δ |
| | | Day 28 | 0.00Δ | 0.00Δ | 2.33* | 0.07Δ | 0.63* | 0.00Δ |
| | IGA3 group | Day 0 | 0.53 | 0.10 | 9.67 | 0.47 | 2.30 | 0.13 |
| | | Day 5 | 0.27* | 0.03Δ | 6.57* | 0.20Δ | 0.90* | 0.07Δ |
| | | Day 28 | 0.17* | 0.33Δ | 5.80* | 0.07* | 1.80Δ | 0.03Δ |
| the acne-removing skincare product of Example 5 | IGA2 group | Day 0 | 0.00 | 0.03 | 5.67 | 0.20 | 2.33 | 0.50 |
| | | Day 5 | 0.00Δ | 0.03Δ | 2.10Δ | 0.03Δ | 1.43Δ | 0.33 |
| | | Day 28 | 0.00Δ | 0.03Δ | 2.17Δ | 0.17Δ | 0.63* | 0.03* |
| | IGA3 group | Day 0 | 0.70 | 0.43 | 10.40 | 0.97 | 2.27 | 0.70 |
| | | Day 5 | 0.33* | 0.23Δ | 6.10* | 0.33* | 1.50Δ | 0.83Δ |
| | | Day 28 | 0.10* | 0.17Δ | 5.63* | 0.27* | 1.20Δ | 0.43Δ |

Note:
rank sum test,
*$p \leq 0.05$,
Δ$p > 0.05$

As shown in Table 4, 5 days after the use of the acne-removing skincare product of Example 4, in IGA2 group, blackhead was improved significantly while no obvious change in other symptoms, compared with basal values; in the subjects of IGA3 group, nodule, papule and blackhead were improved significantly while no obvious change in other symptoms. 28 days after the use of the acne-removing skincare product of Example 4, in the subjects of IGA2 group, papule and blackhead were improved significantly while no obvious change in other symptoms, compared with basal values; in the subjects of IGA3 group, nodule, papule and pustule were improved significantly while no obvious change in other symptoms.

While 5 days after the use of the acne-removing skincare product of Example 5, in IGA2 group, papule was improved significantly while no obvious change in other symptoms, compared with basal values; in the subjects of IGA3 group, nodule, papule and pustule were improved significantly while no obvious change in other symptoms. 28 days after the use of the acne-removing skincare product of Example 5, in the subjects of IGA2 group, papule, blackhead and whitehead were improved significantly while no obvious change in other symptoms, compared with basal values; in the subjects of IGA3 group, nodule, papule and pustule were improved significantly while no obvious change in other symptoms.

3. Pockmark Fading Analysis

Before and after the use of test samples, the skin evenness, clearness and brightness were scored (5-point scale: 1=slight, 5=very obvious). Pockmark fading analysis was performed for the subjects in IGA2 and IGA3 groups before and after 5 days of use of the product. The results were shown in Table 5.

TABLE 5

Pockmark fading analysis

| test samples | | | skin evenness | skin clearness | skin brightness |
|---|---|---|---|---|---|
| the acne-removing skincare product of Example 4 | IGA2 group | Day 0 | 3.40 | 3.48 | 3.48 |
| | | Day 5 | 3.47Δ | 3.48Δ | 3.53Δ |
| | | Day 28 | 3.48Δ | 3.40Δ | 3.42Δ |
| | IGA3 group | Day 0 | 2.75 | 2.63 | 2.90 |
| | | Day 5 | 3.05* | 3.03* | 3.17* |
| | | Day 28 | 3.03Δ | 3.00* | 3.07Δ |

TABLE 5-continued

Pockmark fading analysis

| test samples | | | skin evenness | skin clearness | skin brightness |
|---|---|---|---|---|---|
| the acne-removing skincare product of Example 5 | IGA2 group | Day 0 | 3.33 | 3.30 | 3.38 |
| | | Day 5 | 3.50Δ | 3.57* | 3.53Δ |
| | | Day 28 | 3.38Δ | 3.30Δ | 3.37Δ |
| | IGA3 group | Day 0 | 2.92 | 2.93 | 3.05 |
| | | Day 5 | 3.18* | 3.20* | 3.15Δ |
| | | Day 28 | 3.08Δ | 3.12Δ | 3.20Δ |

Note:
rank sum test,
*$p \leq 0.05$,
Δ$p > 0.05$

As shown in Table 5, 5 days after the use of the acne-removing skincare product of Example 4, in IGA2 group, no significant change in skin evenness, clearness and brightness were observed, compared with basal values, while in IGA3 group, skin evenness, clearness and brightness were all improved significantly. 28 days after the use of the acne-removing skincare product of Example 4, in IGA2 group, no significant change in skin evenness, clearness and brightness were observed, compared with basal values, while in IGA3 group, skin clearness was improved significantly but no obvious change in other parameters.

5 days after the use of the acne-removing skincare product of Example 5, in IGA2 group, skin clearness was improved significantly but no significant change in other parameters, compared with basal values; while in IGA3 group, skin evenness and clearness were improved significantly but no significant change in other parameters. 28 days after the use of the acne-removing skincare product of Example 5, no significant change in skin evenness, clearness and brightness were observed in both IGA2 and IGA3 group, compared with basal values.

3. Severity of the Inflammatory Skin Lesions (Papule, Pustule, Nodule, Cyst)

Before and after 5 days of the use of test samples, severity of the inflammatory skin lesions was observed for the subjects of IGA2 and IGA3 groups. The results were shown in Table 6. (Only the skin lesions which already existed on Day0 were counted; skin lesions appeared after Day0 were not counted.)

TABLE 6

Changes of inflammatory skin lesions

| test samples | | | Grade 0 | Grade 1 | Grade 2 | Grade 3 | Grade 4 |
|---|---|---|---|---|---|---|---|
| the acne-removing skincare product of Example 4 | IGA2 group | Day 0 | 0 | 0 | 30 | 0 | 0 |
| | | Day 5 | 8 | 8 | 14 | 0 | 0 |
| | IGA3 group | Day 0 | 0 | 0 | 0 | 30 | 0 |
| | | Day 5 | 4 | 6 | 19 | 1 | 0 |
| the acne-removing skincare product of Example 5 | IGA2 group | Day 0 | 0 | 0 | 30 | 0 | 0 |
| | | Day 5 | 5 | 14 | 11 | 0 | 0 |
| | IGA3 group | Day 0 | 0 | 0 | 0 | 30 | 0 |
| | | Day 5 | 6 | 2 | 20 | 2 | 0 |

As shown in Table 6, 5 days after the use of the acne-removing skincare product of Example 4, the effective improvement rate of original skin lesions was 53.3% in IGA2 group and 33.3% in IGA3 group, compared with basal values. 5 days after the use of the acne-removing skincare product of Example 5, in IGA2 group, there were 19 people who had improvement in their skin lesions with grade 0 or grade 1 of severity of skin lesion symptoms or with two grades of improvement in severity, compared with basal values. The effective improvement rate was 63.3%. In IGA3 group, there were 8 people who had improvement in their skin lesions with grade 0 or grade 1 of severity of skin lesion symptoms or with two grades of improvement in severity, compared with basal values. The effective improvement rate was 26.7%.

4. Self-Evaluation of Subjects

After the use of product for 5 days and 28 days, questionnaire surveys were carried out in subjects for their satisfaction degree of acne-removing.

4.1 Product satisfaction survey after 5 days of use of the product 5 days after the use of the product, survey was carried out and the subjects scored their satisfaction degree on the product. Assessment criteria: 7=totally satisfied, 1=not satisfied at all. The results were shown in Table 7.

TABLE 7

Product satisfaction degree survey

| | the acne-removing skincare product of Example 4 | | the acne-removing skincare product of Example 5 | |
|---|---|---|---|---|
| test items | IGA2 group | IGA3 group | IGA2 group | IGA3 group |
| color | 5.4 | 5.0 | 5.4 | 5.3 |
| smell | 5.4 | 4.9 | 5.5 | 5.4 |
| texture (viscosity) | 5.8 | 5.3 | 5.9 | 5.5 |
| easy absorption | 5.7 | 5.2 | 5.7 | 5.4 |
| instant relieving effect | 5.3 | 5.3 | 5.5 | 5.2 |
| mildness | 5.8 | 5.1 | 5.6 | 5.6 |

TABLE 7-continued

Product satisfaction degree survey

| | the acne-removing skincare product of Example 4 | | the acne-removing skincare product of Example 5 | |
|---|---|---|---|---|
| test items | IGA2 group | IGA3 group | IGA2 group | IGA3 group |
| acne-removing effect (3 to 5 days) | 4.6 | 4.5 | 5.2 | 4.5 |
| relieving effect on skin discomfort (itch, pain) | 5.5 | 5.0 | 5.9 | 4.3 |
| total satisfaction degree | 5.4 | 5.2 | 5.5 | 5.2 |

As shown in table 7, in IGA2 group, 5 days after the use of the acne-removing skincare product of Example 4, total satisfaction degree was 5.4; 5 days after the use of the acne-removing skincare product of Example 5, total satisfaction degree was 5.5. In IGA3 group, 5 days after the use of the acne-removing skincare product of Example 4, total satisfaction degree was 5.2; 5 days after the use of the acne-removing skincare product of Example 5, total satisfaction degree was 5.2.

4.2 Acne-Removing Satisfaction Degree Survey 28 Says after the Use of the Product 28 days after the use of the product, survey was carried out and the subjects scored their satisfaction degree on acne-removing effect. Assessment criteria: 7=totally satisfied, 1=not satisfied at all. The results were shown in Table 8.

TABLE 8 acne-removing satisfaction degree survey

| | the acne-removing skincare product of Example 4 | | the acne-removing skincare product of Example 5 | |
|---|---|---|---|---|
| test items | IGA2 group | IGA3 group | IGA2 group | IGA3 group |
| pockmark fading effect | 5.1 | 5.0 | 5.2 | 5.0 |
| oil control effect | 5.4 | 5.0 | 5.2 | 5.3 |
| repeated-occurrence-reducing effect | 5.5 | 4.9 | 5.0 | 5.1 |
| total satisfaction degree | 5.5 | 5.1 | 5.2 | 5.2 |

As shown in table 8, in IGA2 group, 28 days after the use of the acne-removing skincare product of Example 4, total satisfaction degree was 5.5; 28 days after the use of the acne-removing skincare product of Example 5, total satisfaction degree was 5.2. In IGA3 group, 28 days after the use of the acne-removing skincare product of Example 4, total satisfaction degree was 5.2; 28 days after the use of the acne-removing skincare product of Example 5, total satisfaction degree was 5.2.

4.3 Product Property Survey 5 Days after the Use of the Product 5 days after use of the product, survey was carried out and the subjects scored the product property. The results were shown in Table 9.

Assessment Criteria:

paint experience of the acne-removing essence: 1-very difficult to paint, 2-quite difficult to paint, 3-just right, 4-easy to paint, 5-very easy to paint;

texture of the acne-removing essence: 1-too watery, 2-a little bit watery, 3-just right, 4—a little bit sticky, 5-too sticky;

actual onset time of acne-removing: 1-more than one week, 2-within one week, 3—within 5 days, 4—within 3 to 4 days, 5—within 1 to 2 days.

TABLE 9

Product properties survey

| test items | product properties | IGA grade | 1 score | 2 score | 3 score | 4 score | 5 score |
|---|---|---|---|---|---|---|---|
| the acne-removing skincare product of Example 4 | paint experience | IGA2 | 0.0% | 10.0% | 20.0% | 43.3% | 26.7% |
| | | IGA3 | 0.0% | 3.3% | 43.3% | 36.7% | 16.7% |
| | texture | IGA2 | 0.0% | 6.7% | 80.0% | 13.3% | 0.0% |
| | | IGA3 | 0.0% | 20.0% | 60.0% | 20.0% | 0.0% |
| | actual onset time of acne-removing | IGA2 | 26.7% | 30.0% | 13.3% | 20.0% | 10.0% |
| | | IGA3 | 26.7% | 33.3% | 16.7% | 23.3% | 0.0% |
| the acne-removing skincare product of example 5 | paint experience | IGA2 | 0.0% | 0.0% | 36.7% | 36.7% | 26.7% |
| | | IGA3 | 0.0% | 3.3% | 23.3% | 56.7% | 16.7% |
| | texture | IGA2 | 0.0% | 20.0% | 70.0% | 6.7% | 3.3% |
| | | IGA3 | 3.3% | 30.0% | 63.3% | 3.3% | 0.0% |
| | actual onset time of acne-removing | IGA2 | 16.7% | 30.0% | 16.7% | 36.7% | 0.0% |
| | | IGA3 | 23.3% | 26.7% | 30.0% | 20.0% | 0.0% |

4.4 Survey of Satisfaction Degree on Adverse Reactions 5 Days after the Use of the Product 5 days after use of the product, survey was carried out and the subjects scored their satisfaction degree on the adverse reactions of the product. The results were shown in Table 10. Assessment criteria: 1=very severe, 7=none.

TABLE 10 survey of satisfaction degree of adverse reactions

| test items | adverse reactions | IGA | 1 | 2 | 3 | 4 | 5 | 6 | 7 | Complete satisfaction % |
|---|---|---|---|---|---|---|---|---|---|---|
| the acne-removing skincare product of Example 4 | redness | IGA2 | 1 | 0 | 0 | 1 | 0 | 1 | 27 | 90.0% |
| | | IGA3 | 0 | 1 | 0 | 5 | 3 | 3 | 18 | 60.0% |
| | fever | IGA2 | 0 | 0 | 1 | 2 | 0 | 1 | 26 | 86.7% |
| | | IGA3 | 0 | 1 | 1 | 1 | 5 | 2 | 20 | 66.7% |
| | swelling | IGA2 | 0 | 1 | 0 | 0 | 0 | 1 | 28 | 93.3% |
| | | IGA3 | 0 | 1 | 0 | 2 | 3 | 3 | 21 | 70.0% |
| | itch | IGA2 | 0 | 1 | 0 | 0 | 1 | 0 | 28 | 93.3% |
| | | IGA3 | 0 | 1 | 1 | 4 | 4 | 4 | 16 | 53.3% |
| | pain | IGA2 | 0 | 1 | 0 | 1 | 0 | 1 | 27 | 90.0% |
| | | IGA3 | 0 | 0 | 1 | 4 | 2 | 2 | 21 | 70.0% |
| the acne-removing skincare product of Example 5 | redness | IGA2 | 0 | 0 | 0 | 1 | 2 | 1 | 26 | 86.7% |
| | | IGA3 | 0 | 1 | 0 | 0 | 0 | 3 | 26 | 86.7% |
| | fever | IGA2 | 0 | 0 | 0 | 1 | 1 | 1 | 27 | 90.0% |
| | | IGA3 | 0 | 0 | 1 | 0 | 0 | 2 | 27 | 90.0% |
| | swelling | IGA2 | 0 | 1 | 0 | 0 | 2 | 3 | 24 | 80.0% |
| | | IGA3 | 1 | 0 | 0 | 0 | 0 | 2 | 27 | 90.0% |
| | itch | IGA2 | 0 | 0 | 1 | 1 | 0 | 1 | 27 | 90.0% |
| | | IGA3 | 2 | 0 | 0 | 1 | 2 | 2 | 23 | 76.7% |
| | pain | IGA2 | 0 | 0 | 1 | 0 | 0 | 2 | 27 | 90.0% |
| | | IGA3 | 1 | 0 | 0 | 0 | 0 | 2 | 27 | 90.0% |

5. Assay of Melanin and Heme in Skin

Skin melanin and heme assay was conducted by using detector Mexameter MX18 to detect the content of melanin and heme in skin. The results were shown in Table 11. Skin melanin value serves as a general standard for judging skin black and white. The whiter the skin color is, the less melanin level. Skin heme serves as a general standard for judging skin red and white. The redder the skin color is, the higher heme level.

TABLE 11

Skin melanin and heme value

| test items | | test time | test position | | control position | |
|---|---|---|---|---|---|---|
| | | | melanin | heme | melanin | heme |
| the acne-removing skincare product of Example 4 | IGA2 group | D0 | 179 | 400 | 156 | 373 |
| | | D28 | 199 | 335 | 165 | 326 |
| | | p | * | * | Δ | * |
| | IGA3 group | D0 | 193 | 422 | 165 | 361 |
| | | D28 | 210 | 386 | 180 | 357 |
| | | p | Δ | * | Δ | Δ |
| the acne-removing skincare product of Example 5 | IGA2 group | D0 | 191 | 393 | 163 | 333 |
| | | D28 | 211 | 342 | 171 | 319 |
| | | p | * | * | Δ | Δ |
| | IGA3 group | D0 | 199 | 441 | 175 | 355 |
| | | D28 | 225 | 375 | 186 | 343 |
| | | p | * | * | * | Δ |

Note:
rank sum test,
* $p \leq 0.05$,
Δ $p > 0.05$

As shown in Table 11, 28 days after the use of the acne-removing skincare product of Example 4, in IGA2 group, skin melanin value increased significantly and heme value decreased significantly in the test position, compared with basal value; while in control position, melanin value did not change significantly and heme value decreased significantly. In IGA3 group, melanin value did not change significantly and heme value decreased significantly in test position; while in control position, neither melanin nor heme value changed significantly. While 28 days after the use of the acne-removing skincare product of Example 5, in IGA2 group, skin melanin value increased significantly and heme value decreased significantly in test position; while in control position, neither melanin nor heme value changed significantly. In IGA3 group, melanin value changed significantly and heme value decreased significantly in test position; while in control position, melanin value changed significantly and heme value did not change significantly.

6. Skin Adverse Reactions

During the use of the acne-removing skincare product of Example 4 and the acne-removing skincare product of Example 5, no local skin adverse reactions, such as red spots, papules, wheals, swellings or system skin adverse reactions were observed in the subjects.

The invention claimed is:

1. An acne-removing skincare product, comprising an acne-removing composition, wherein the acne-removing composition is made from mangosteen pericarp, thyme and Fructus aurantii in a weight ratio of (6 to 8):(1 to 2):(1 to 2), and consists of mangosteen pericarp extract, thyme extract and Fructus aurantii extract.

2. The acne-removing skincare product of claim 1, which further comprises acne-removing compound preparation and tea tree essential oil, wherein the acne-removing compound preparation consists of the following components:

| Components | Amount |
| --- | --- |
| propylene glycol | 73.2% |
| water | 15% |
| OLDENLANDIA DIFFUSA extract | 2.5% |
| LONICERA JAPONICA extract | 3% |
| SALVIA MILTIORRHIZA ROOT extract | 2.5% |
| GLEDITSIA AUSTRALIS SEED extract | 3% |
| methylparaben | 0.1% |
| phenoxyethanol | 0.7%. |

3. The acne-removing skincare product of claim 2, wherein the weight ratio of the acne-removing composition consisting of mangosteen pericarp extract, thyme extract and Fructus aurantii extract, acne-removing compound preparation, and tea tree essential oil is (1 to 5):(2 to 10):(0.05 to 0.1), wherein the acne-removing compound preparation consists of the following components:

| Components | Amount |
| --- | --- |
| propylene glycol | 73.2% |
| water | 15% |
| OLDENLANDIA DIFFUSA extract | 2.5% |
| LONICERA JAPONICA extract | 3% |
| SALVIA MILTIORRHIZA ROOT extract | 2.5% |
| GLEDITSIA AUSTRALIS SEED extract | 3% |
| methylparaben | 0.1% |
| phenoxyethanol | 0.7%. |

4. The acne-removing skincare product according to claim 1, which further comprises at least one of a solvent, a thickener, a conditioner, a humectant, a pH regulator, a surfactant and a freshener.

5. The acne-removing skincare product of claim 4, wherein the solvent is at least one of water, propylene glycol, butylene glycol, glycerol and pentylene glycol;
the thickener is at least one of poly(acrylic acid and hydroxyethyl acrylate/sodium acryloyldimethyl taurate copolymer;
the conditioner is at least one of allantoin, vitamin A palmitate, dipotassium glycyrrhizinate, Centella asiatica extract, nicotinamide, octanoylglycine, quaternary ammonium salt-73, salicylic acid, and octanoylsalicylic acid;
the humectant is at least one of ethylhexylglycerin, butylene glycol, 1,2-pentylene glycol, glycerol, propylene glycol, sodium hyaluronate, D-panthenol and sodium pyrrolidone carboxylate;
the pH regulator is at least one of sodium hydroxide, potassium hydroxide, arginine, citric acid and sodium citrate;
the surfactant is at least one of tween-20, PEG-40 hydrogenated castor oil and PEG-60 hydrogenated castor oil; and
the freshener is at least one of menthol, mint essential oil and menthol lactate.

6. The acne-removing skincare product of claim 4, comprising:

| | |
| --- | --- |
| the acne-removing composition consisting of mangosteen pericarp, thyme, and Fructus aurantii | 1 wt %-5 wt % |
| acne-removing compound preparation | 2 wt %-10 wt % |
| tea tree essential oil | 0.06 wt % |
| acrylates/$C_{10}$-$C_{30}$ alkyl acrylate | 0.45 wt % |
| hydroxyethyl | 1.2 wt % |
| allantoin | 0.1-0.3 wt % |
| vitamin A palmitate | 0 wt %-0.5 wt % |
| dipotassium glycyrrhizinate | 0-0.3 wt % |
| Centella asiatica extract | 0-0.5 wt % |
| nicotinamide | 0.5 wt %-3 wt % |
| Butylene glycol | 1 wt %-5 wt % |
| pentylene glycol | 0.5 wt %-3 wt % |
| sodium hydroxide | 0.15 wt % |
| tween-20 | 0-1 wt % |
| cooling complex | 0-0.1 wt % |
| propylene glycol | 0-8 wt % |
| water | making up to 100 | wherein the acne-removing compound preparation consists of the following components:

| Components | Amount |
| --- | --- |
| propylene glycol | 73.2% |
| water | 15% |
| OLDENLANDIA DIFFUSA extract | 2.5% |
| LONICERA JAPONICA extract | 3% |
| SALVIA MILTIORRHIZA ROOT extract | 2.5% |
| GLEDITSIA AUSTRALIS SEED extract | 3% |
| methylparaben | 0.1% |
| phenoxyethanol | 0.7%. |

7. A method for preparing an acne-removing skincare product, comprising the following steps:

1) acrylates/$C_{10}$-$C_{30}$ alkyl acrylate cross-linked polymer, allantoin and allantoin are taken and dissolved completely by adding water, then heated to 70° C.~95° C. to obtain a first reaction solution;

2) acne-removing compound preparation and an acne-removing composition consisting of mangosteen pericarp extract, thyme extract and Fructus aurantii extract are dissolved by adding water and propylene glycol, respectively, then added into the first reaction solution at 80° C., mixed to dissolved completely to obtain a second reaction solution;

3) sodium hydroxide is added to the second reaction solution, and mixed evenly to obtain a third reaction solution;

4) butylenes glycol and vitamin A palmitate are added to the third reaction solution and mixed, the temperature is reduced to 45° C., and a forth reaction solution is obtained;

5) pentylene glycol, cooling complex and tea tree essential oil are mixed and dissolved, then added into the forth reaction solution, mixed evenly, to obtain a fifth reaction solution; and 6) dipotassium glycyrrhizinate, Centella asiatica extract and nicotinamide are dissolved by adding water, then added into the fifth reaction solution, and mixed evenly, wherein the acne-removing compound preparation consists of the following components:

| Components | Amount |
|---|---|
| propylene glycol | 73.2% |
| water | 15% |
| OLDENLANDIA DIFFUSA extract | 2.5% |
| LONICERA JAPONICA extract | 3% |
| SALVIA MILTIORRHIZA ROOT extract | 2.5% |
| GLEDITSIA AUSTRALIS SEED extract | 3% |
| methylparaben | 0.1% |
| phenoxyethanol | 0.7%. |

\* \* \* \* \*